United States Patent
Park et al.

(10) Patent No.: US 6,958,427 B2
(45) Date of Patent: Oct. 25, 2005

(54) METHOD FOR CATALYTIC DEHYDROGENATION OF HYDROCARBONS USING CARBON DIOXIDE AS A SOFT OXIDANT

(75) Inventors: Sang-Eon Park, Daejon (KR); Jong-Son Chang, Daejon (KR); Min Seok Park, Daejon (KR)

(73) Assignee: Korea Research Institute of Chemical Technology (KR)

( * ) Notice: Subject to any disclaimer, the term of this patent is extended or adjusted under 35 U.S.C. 154(b) by 0 days.

(21) Appl. No.: 10/376,322

(22) Filed: Mar. 3, 2003

(65) Prior Publication Data

US 2003/0166984 A1 Sep. 4, 2003

(30) Foreign Application Priority Data

Mar. 4, 2002 (KR) .............................. 10-2002-0011418

(51) Int. Cl.[7] ............................................... C07C 4/06
(52) U.S. Cl. ..................................................... 585/444
(58) Field of Search ................................. 585/444, 445

(56) References Cited

U.S. PATENT DOCUMENTS

| | | | |
|---|---|---|---|
| 4,246,421 A | 1/1981 | Bartek et al. |
| 4,255,283 A | 3/1981 | Bartek et al. |
| 4,418,237 A | 11/1983 | Imai |
| 4,435,607 A | 3/1984 | Imai |
| 4,717,779 A | 1/1988 | Bricker et al. |
| 6,034,032 A | 3/2000 | Park et al. |
| 6,037,511 A | 3/2000 | Park et al. |

FOREIGN PATENT DOCUMENTS

| | | |
|---|---|---|
| EP | 0 438 902 A2 | 7/1991 |
| GB | 2 201 159 A | 8/1988 |

OTHER PUBLICATIONS

Jong–San Chang, et al., "Effect of Carbon Dioxide in Dehydrogenation of Ethylbenzene to Styrene over Zeolite–Suported Iron Oxide Catalyst," Bull. Korean Chem. Soc., vol. 19 No. 12, pp 1342–1346 (1998).

Junshi Matsui, Toshiaki Sodesawa and Fumio Nozaki, "Influence of carbon dioxide addition upon decay of activity of a potassium–promoted iron oxide catalyst for dehydrogenation of ethylbenzene," Applied Catalysis 67, (1991), pp. 1979–188.

Mitsuo–o Sugino, Hiroshi Shimada, Tadotoshi Turuda, Hidetoshi Miura, Naoki Ikenaga, Toshimitsu Suzuki, "Oxidative dehydrogenation of ethylbenzene with carbon monoxide," Applied Catalysis A: General 121, (1995), pp. 125–137.

Naoki Mimura and Masahiro Saito, "Dehydrogenation of ethylbenzene to styrene over $Fe_2O_3/Al_2O_3$ catalysts in the presence of carbon dioxide," Catalysis Letters 58, (1999), pp. 59–62.

Yoshihiro Sakurai, Takamasa Suzaki, Na–oki Ikenaga, Toshimitsu Suzuki, "Dehydrogenation of ethylbenzene with an activated carbon–supported vanadium catalyst," Applied Catalysis A: General 192, (2000), pp. 281–288.

*Primary Examiner*—Thuan D Dang
(74) *Attorney, Agent, or Firm*—Finnegan, Henderson, Farabow, Garrett & Dunner, L.L.P.

(57) ABSTRACT

The present invention relates to a method for catalytic dehydrogenation of alkylaromatic hydrocarbons and more particularly, to a method for catalytic dehydrogenation of alkylaromatic hydrocarbons using carbon dioxide as a soft oxidant in the presence of a heterogeneous catalyst comprising both vanadium and iron, which allows operation at a lower reaction temperature due to improve thermodynamic equilibrium and provides an enhanced conversion of hydrocarbons and energy saving.

10 Claims, 1 Drawing Sheet

TC: Thermocouple

METHOD FOR CATALYTIC DEHYDROGENATION OF HYDROCARBONS USING CARBON DIOXIDE AS A SOFT OXIDANT

FIELD OF THE INVENTION

The present invention relates to a method for catalytic dehydrogenation of alkylaromatic hydrocarbons, and more particularly, to a method for catalytic dehydrogenation of alkylaromatic hydrocarbons using carbon dioxide as a soft oxidant in the presence of a heterogeneous solid catalyst which contains both vanadium and iron as active components, which allows a reaction at a relatively lower temperature due to improved thermodynamic equilibrium, and therefore provides an enhanced reactant conversion and energy saving.

BACKGROUND OF THE INVENTION

Aromatic olefin compounds have been widely used as monomers of polymers or raw materials in the chemical industry. These aromatic olefin compounds have been generally prepared by a dehydrogenation of alkylaromatic hydrocarbons. Usually productivity or selectivity associated with the dehydrogenation is dependent upon the role of hydrocarbons or catalysts. Various diluents or oxidants have been selected and used to prevent deactivation of a catalyst by coke formation and to improve the lifetime of a catalyst in the dehydrogenation. For example, steam is widely used as a diluent to improve activity of a catalyst and the lifetime thereof in the dehydrogenation of aromatic hydrocarbons such as ethylbenzene. Despite a disadvantage in view of thermodynamic equilibrium, hydrogen is usually used as a diluent in the dehydrogenation of hydrocarbons having $C_3$, $C_4$, and $C_8$–$C_{12}$ to prevent severe coke deposition on the catalyst thereby increasing the lifetime of a catalyst. Further, air or oxygen is used as an oxidant in the dehydrogenation of 1-butene to 1,3-dibutadiene.

Ethylbenzene dehydrogenation, the most widely used dehydrogenation process at present, produces styrene which is a very useful compound in petrochemical industry to be used as a monomer or a starting material for the synthesis of synthetic rubbers, ABS resins, polystyrenes and the like. Its demand is on rapid increase. Styrene has been mainly produced by ethylbenzene dehydrogenation in the presence of an iron oxide catalyst with excess supply of steam to ethylbenzene. Typical catalysts used in the dehydrogenation of ethylbenzene are K—$Fe_2O_3$ catalysts. However, there are a few problems associated with the dehydrogenation of ethylbenzene. The ethylbenzene dehydrogenation results in a great deal amount of energy loss in the course of condensing steam used in excess prior to separating the target product from the dehydrogenation. Further, ethylbenzene dehydrogenation is much limited in obtaining a high yield of styrene due to thermodynamic limitation of endothermic reaction.

Therefore, various methods have been attempted to overcome the above-mentioned problems associated with the use of steam during the dehydrogenation of ethylbenzene. The first method involves combining the dehydrogenation of ethylbenzene and the selective oxidation reaction of hydrogen. In this method, the dehydrogenated hydrogen is oxidized by oxygen in order to supply the heat of reaction and to modify the reaction equilibrium, if deemed necessary. Bricker et al. have disclosed a combined process of the dehydrogenation of ethylbenzene and the oxidation reaction of the dehydrogenated hydrogen, performed in the presence of dual catalysts of a dehydrogenation catalyst and a platinum oxidation catalyst in U.S. Pat. No. 4,717,779. U.S. Pat. Nos. 4,418,237 and 4,435,607, assigned to UOP (US), disclose a process for the dehydrogenation of ethylbenzene with a dehydrogenation catalyst in the presence of steam and a selective oxidation of hydrogen in the presence of an oxidation catalyst. In these methods, hydrocarbons are treated with steam and a dehydrogenation catalyst along with a subsequent or concurrent treatment with an oxidation catalyst. It was further suggested that 'SMART process', which combines the fundamental concept of UOP and the technology of Lummus, be used with the enhanced process of dehydrogenation of ethylbenzene. However, since there is a danger of explosion with use of oxygen in the oxidative dehydrogenation, these methods have not been yet applied practically.

The second method involves lowering the reaction temperature by means of oxidative dehydrogenation via molecular oxygen, thereby converting the endothermic reaction to one of exothermic reaction. U.S. Pat. Nos. 4,255,283 and 4,246,421 as assigned to the Standard Oil Company disclose an oxydehydrogenation process for ethylbenzene to styrene in the presence of a metal phosphate catalyst composition. There have been reported that zirconium phosphate, cerium phosphate, and carbon molecular sieve as catalysts are used at a temperature of from 300° C. to 500° C. in the oxydehydrogenation of ethylbenzene. However, there is a danger of explosion with use of molecular oxygen, and the selectivity is reduced due to the side reaction of the complete oxidation, partial oxidation, cracking and the like.

The third method, the application of a catalytic inorganic membrane reactor, can improve the conversion of ethylbenzene by favorably shifting the reaction equilibrium and lowering the reaction temperature. In particular, GB Patent No. 2,201,159 suggests the use of a ceramic membrane, which is selectively permeable to hydrogen, can effectively separate hydrogen among the dehydrogenated products. EP Patent No. 438,902 A2 discloses a solid multi-component membrane for use in an electrochemical reactor characterized by a mixed metal oxide material having a perovskite structure. The method is superb in principle but has several disadvantages with use of an inorganic membrane reactor for the expensive construction costs of facilities, and the inefficient heat and material transfer. Thus, it is not suitable for industrial applications.

Therefore, economic and safe dehydrogenation processes of alkylaromatic hydrocarbons are highly demanded which would be able to alleviate the limited equilibrium and to diminish energy consumption with the use of carbon dioxide instead of excess steam.

The present invention introduces a dehydrogenation process of alkylaromatic hydrocabons including ethylbenzene by employing carbon dioxide as an oxidant. Recently, there has been a growing concern of carbon dioxide to be responsible for the global warming caused by the "greenhouse effect". For the mitigation of global warming due to carbon dioxide, catalytic conversion of $CO_2$ has been extensively studied for the last decade. Most of studies on this field have been concentrated on the utilization of carbon dioxide as a carbon source through catalytic reduction processes with hydrogen as a reductant. However, the catalytic hydrogenation is confronted with some limitations to be commercialized due to the use of expensive hydrogen. On the other hand if carbon dioxide is used efficiently as an oxidant, instead of steam, in the dehydrogenation of hydrocarbons such as ethylbenzene, the dehydrogenation process would be a useful and economical process for saving energy.

However, a small amount of carbon dioxide in ethylbenzene dehydrogenation is known to inhibit the catalytic activity of a dehydrogenation catalyst comprising iron oxide as a major component and K—$Fe_2O_3$ as an active oxide component due to the decomposition of active phase in the presence of carbon dioxide (*Appl. Catal.*, 67, 179 (1991)). Thus, use of carbon dioxide was largely limited in the process for preparing styrene by using steam dehydrogenation reaction due to its property of deactivating a catalyst. Carbon dioxide decomposes ferrite compounds, such as $K_2Fe_2O_3$ or $K_2Fe_{22}O_{34}$ or used as ethylbenzene dehydrogenation catalysts, to $K_2CO_3$ and $Fe_2O_3$ having much lower activity. It was necessary to utilize catalysts to retain sufficient activity and selectivity when using carbon dioxide in the dehydrogenation process of hydrocarbons. As a result, the inventors of the present invention have already disclosed catalysts supported by iron oxides to increase the catalytic activity with carbon dioxide in the dehydrogenation of hydrocarbons in U.S. Pat. Nos. 6,037,511 and 6,034,032. Sugino et al. reported that the activity of dehydrogenation of ethylbenzene was significantly improved under the flow of carbon dioxide by means of a catalyst having an active carbon carrier impregnated with lithium ferrite oxide (Appl. Catal., 121, 125 (1995)). There are others which also reported that the enhancement effects of the dehydrogenation activity of ethylbenzene were significant with carbon dioxide in the presence of $Fe_2O_3/Al_2O_3$ catalyst (*Catal. Lett.*, 58, 59 (1999)) and an activated carbon-supported vanadium catalyst (*Appl. Catal. A.*, 192, 281 (2000)).

Meanwhile, in recent years, it has been noted that carbon dioxide is not a waste but a useful chemical resource. Therefore, it is a key issue to know how to economically obtain large amount of carbon dioxide to be practically applied for the chemical process. It is under extensive researches to develop how to reduce the volume of carbon dioxide released into the atmosphere since carbon dioxide is thought to be responsible for the global warming caused by the "greenhouse effect". Conventionally, as a method for separating carbon dioxide gas from an effluent or an exhaust gas, an absorption method is being widely used in the petrochemical process, and a membrane separation method or the like are proposed. However, it is most desirable to directly apply carbon dioxide gas discharged from the exhaust to the reaction process instead of using pure carbon dioxide separated and purified with respect to cost reduction. It is quite normal that a relatively large quantity of carbon dioxide is produced in the field of petrochemical industry. Therefore, it will be highly advantageous in many respects such as transport charges, reduction of expenditure and the like if facilities to perform the dehydrogenation are built in an area adjacent to the release of carbon dioxide.

SUMMARY OF THE INVENTION

The present invention has been completed by establishing optimum reaction conditions for the dehydrogenation of alkylaromatic hydrocarbons by directly using carbon dioxide discharged from petrochemical processes, wherein carbon dioxide serves as an oxidant, unlike the conventional way of using steam, and also employing a heterogeneous solid catalyst which contains both vanadium and iron as active components. Accordingly, an object of the present invention is to provide a process for catalytic dehydrogenation of alkylaromatic hydrocarbons using carbon dioxide released from the petrochemical process as a soft oxidant.

BRIEF DESCRIPTION OF THE INVENTION

DETAILED DESCRIPTION OF THE INVENTION

Figure 1:
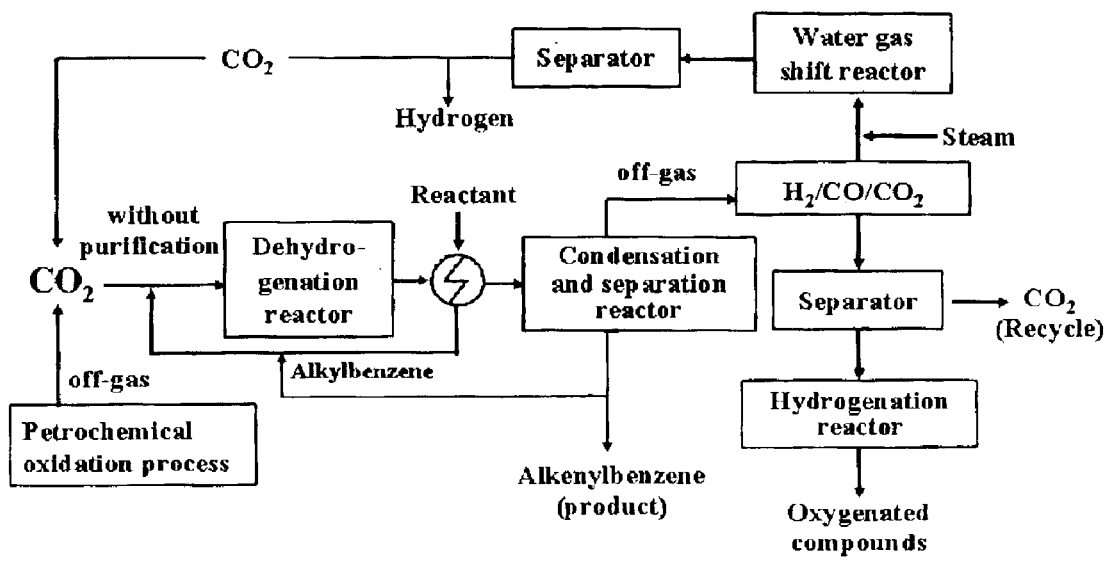
FIG. 1 is a schematic diagram of the dehydrogenation process of hydrocarbons using carbon dioxide as an oxidant according to the present invention.

As set forth hereinabove, the present invention relates to a process for the dehydrogenation of alkylaromatic hydrocarbons using carbon dioxide as an oxidant in the presence of a heterogeneous solid catalyst which contains both vanadium and iron as active components.

The dehydrogenation process of the present invention may be applied to various alkylaromatic hydrocarbons such as cumene and dialkylbenzene including ethylbenzene. Carbon dioxide used in the dehydrogenation of the present invention may be a crude form of carbon dioxide discharged from petrochemical processes as well as those with high purity. One of typical petrochemical processes discharging carbon dioxide is an oxidation reaction of ethylene to produce ethylene oxide. Carbon dioxide gas is inevitably produced as a by-product from this reaction, where it is necessary to separate carbon dioxide for purifying ethylene oxide as a desired product. The separated carbon dioxide is relatively highly concentrated and mostly discarded without being used for particular purposes except the use for producing dry ice. Carbon dioxide produced from the manufacturing process of ethylene oxide can be utilized without going through with any purification process for the dehydrogenation process, which is the superiority of the present invention. The concentration of carbon dioxide contained in the carbon dioxide produced in the course of manufacturing ethylene oxide is in the range of from 50% to 99.9%, and steam, oxygen and the like account for the rest. Utilization of carbon dioxide in the dehydrogenation process of hydrocarbons according to the present invention provides several advantages as follows: a remarkable decrease in energy loss due to the use of carbon dioxide as an oxidant instead of excess steam; a shift in the equilibrium towards improved conversion of the dehydrogenation reaction so as to get high activity as compared to commercial process using steam as a diluent. Sufficient catalytic activity in the dehydrogenation reaction of alkylaromatic hydrocarbons can be obtained at a temperature lower than that of conventional processes by 30–50° C. The oxygen species dissociated from carbon dioxide on the catalyst surface derives the reaction with the hydrogen leaving from hydrocarbons and, therefore, accelerates the reaction process like the oxidative dehydrogenation using oxygen. Thus, the reaction equilibrium can be remarkably increased as compared to that of the conventional dehydrogenation process of hydrocarbons using steam. Further, in the dehydrogenation of hydrocarbons of the present invention using carbon dioxide discharged from petrochemical processes, there are advantages in the respect of not only the energy saving but also the improving productivity of alkenylaromatic hydrocarbons.

As mentioned above, the enforceability of the present invention to perform the dehydrogenation reaction using carbon dioxide is in part attributed to the appropriate selection of a catalyst, wherein the catalyst is a heterogeneous solid catalyst consisting of both vanadium and iron as active components. Preferably, the catalyst used in the present invention can further comprise, in addition to the active metals of vanadium and iron, other promoters for the purpose of increasing activity as well as stability selected from the group consisting of antimony, tin, potassium, magnesium, lanthanum, chromium, cerium, molybdenum, calcium, manganese, zirconium, and cesium. The metals contained in the heterogeneous solid catalyst of the present invention are basically in the form of oxides, and these metal oxides can be used for the catalysts wherein the metal oxides are highly dispersed on the carriers with large surface area or the metal oxides can be used in the form of a composite between the oxides and carriers. The carriers are preferred to be selected from alumina, zirconia, alumina modified with metals and zirconia modified with metals to improve the conversion and selectivity. The metals that decorate alumina, used as a carrier, are selected from the group consisting of magnesium, calcium, barium, zirconium, lanthanum, cerium, yttrium and niobium. For the proper activation of the heterogeneous catalyst of the present invention, the contents of vanadium and iron in the oxides as active components are preferred to be varied in the range of from 0.1 to 30 wt. % and from 0.1 to 30 wt. %, respectively, in the catalyst. The contents of other metals in the oxides as coactive metals are preferred to be varied in the range of from 0 to 30 wt. % in the catalyst. The reaction conditions were set as follows: (1) the weight hourly space velocity (WHSV), i.e., the weight ratio of reactants supplied per unit weight of a catalyst per unit hour, was set to be in the range of 0.1–10 per hour; (2) reactants were added into a reactor, wherein the molar ratio between carbon dioxide and alkylbenzene was set to be in the range of 0.5–20:1; and (3) reaction pressure was adjusted in the range of 0.5–2 atm.

FIG. 1 represents a schematic diagram of the dehydrogenation process of hydrocarbons using carbon dioxide as an oxidant according to the present invention. The dehydrogenation process of hydrocarbons can be divided to four steps: (1) supplying carbon dioxide; (2) dehydrogenation reaction of hydrocarbons; (3) separation of a dehydrogenated product; and (4) recycling of a mixture of gases released from the separation step.

Carbon dioxide is directly supplied from gases discharged from the petrochemical process without requiring any additional purification process in the first step. The typical petrochemical process is a manufacturing process of ethylene oxide by partial oxidation of ethylene. The second dehydrogenation step is performed by transferring carbon dioxide gas released from the oxidation process through a pipe line with a hydrocarbon compound to a reactor in the presence of a catalyst. The dehydrogenated liquid and gases are separated by condensation and separation processes and the olefin compound, unreacted reactant and byproducts are purified by distillation. The recycling process of the gas mixture is performed by one of the following two processes: (1) steam is added to a gas mixture containing hydrogen, carbon monoxide and carbon dioxide as major components to convert steam and carbon monoxide into carbon dioxide and hydrogen via water gas shift reaction, which are then separated from the mixture and the separated carbon dioxide is recycled for further dehydrogenation reaction; and (2) carbon dioxide is separated from a gas mixture containing hydrogen, carbon monoxide and carbon dioxide as major components and the rest is then transferred to a catalytic hydrogenation reactor to produce oxygenated compounds such as methanol and dimethyl ether. The separated carbon dioxide is recycled for further dehydrogenation reaction. A molar ratio of hydrogen and carbon monoxide produced from the dehydrogenation process is in the range of from 0.5 to 2.0, which is appropriate to apply for manufacturing oxygen-containing compounds.

Figure 2:
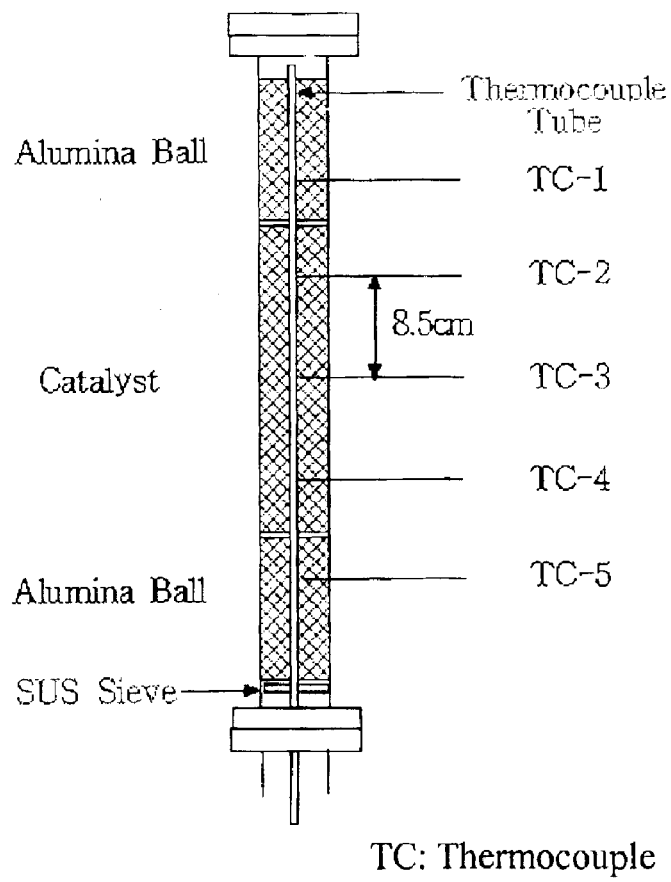
FIG. 2 is a schematic diagram of a tubular reactor used to test the catalytic activities in the dehydrogenation of hydrocarbons using carbon dioxide as an oxidant according to the present invention.

In the present invention, a microcatalytic testing unit of a laboratory scale and a reaction apparatus for mini-pilot scale were utilized for examining the activity and selectivity of the heterogeneous solid catalyst in the present invention for the dehydrogenation of hydrocarbons with carbon dioxide as an oxidant. FIG. 2 represents a schematic diagram of a tubular reactor in the reaction apparatus for mini-pilot scale used to test the catalytic activities in the dehydrogenation of hydrocarbons using carbon dioxide as an oxidant according to the present invention. The reactor used was made of Hastalloy C for high temperatures with 25 mm in diameter of and 80 cm in length. 100 mL of the catalyst was placed into a catalyst reactor to test and a height of the catalyst bed was set to be about from 25 to 30 cm in height even though it varied depending on specific gravity of each catalyst. The liquid alkylaromatic hydrocarbon was supplied by means of a metering pump. Alkylaromatic hydrocarbon as a reactant and carbon dioxide as both oxidant and diluent had been mixed and pre-heated before the reactant was supplied into the reactor. The liquid alkylaromatic hydrocarbon was vaporized when it reached the pre-heater by heating the connecting line from the site of the pump. The vaporized reactant sufficiently heated in the pre-heater was placed in the reactor and the catalytic reaction was performed at a predetermined temperature. Five heaters having 15 cm of length were installed from top to bottom of the reactor in a row to minimize temperature gradient. Each heater was separately controlled to have the same temperature in the catalyst bed. Some of the products from the reactor were stored in a sampling tank while some were directly transferred into a final storage tank. Referring to the microcatalytic testing unit for a laboratory scale, there was a vertically installed fixed bed reactor made of quartz or stainless steel with 12 mm of internal diameter, 350 mm of height, and the reaction temperature was adjusted within the range of 400° C.–700° C. by using electric heaters and programmable temperature controller. The dehydrogenation catalyst prepared in the present invention was filled into a reactor at the size of 100 mesh and pretreated for 1 hour at 600° C. with nitrogen gas prior to performing a reaction, and alkylbenzene, a reactant, was passed through the catalyst bed using a liquid metering pump under the atmosphere of carbon dioxide. The flow rate of carbon dioxide was adjusted with mass flow controller. It was mixed with alkylbenzene in a mixing chamber and the reactant mixture was preheated at 500° C. in a preheater before passing through the reactor.

On the other hand, a steam supplier consisting of a metering pump to supply water and an electric heater was also installed to the reactor in order to compare characteristics of the dehydrogenation reaction using carbon dioxide to those of the conventional dehydrogenation reaction using steam. The reactants and products were analyzed by two gas chromatographs (Chrompack CP 9001) equipped with flame ionization detector and thermal conductivity detector, respectively.

The present invention will now be explained in more detail with reference to the following examples, but it is to be understood that the present invention is not restricted thereto and various modifications are possible within the scope of the invention.

EXAMPLE 1

Example 1 is a dehydrogenation reaction of ethylbenzene to styrene using carbon dioxide in the presence of a catalyst having a spherical shape of 3 mm in size wherein vanadium, iron and antimony are impregnated onto a zirconia-alumina support that contains 10 wt. % of zirconia (hereinafter referred to as V—Fe—Sb/$ZrO_2$—$Al_2O_3$). The catalyst used in Example 1 was prepared from $SbCl_3$ precursor by using a zirconia-alumina support via sol-gel method (diameter: 3 mm; BET specific surface area: 165 m²/g). The contents of vanadium, iron and antimony in the above catalyst were used in the range of 1–15 wt. %, 1–15 wt. % and 20 wt. %, respectively, based on oxides. The catalyst were prepared by the following method: all the precursors of the constituents of the catalyst except support were dissolved in distilled water at 25° C. so that the concentration of metals became 1 M. Tartaric acid having the same mole as those of added metal salts was added to the mixture and dissolved completely for 2 hours at the same temperature. Ethylene glycol having the same moles as those of added metal salts was added to the mixture and the mixture was stirred for 2 hours at 25° C. Zirconia-alumina support was added to the solution mixture with stirring so that the ratio of the zirconia-alumina support based on solid content becomes 1:5. The solvent in the mixture was evaporated using a rotary evaporator under reduced pressure at 80–100° C. Then the catalyst powder was dried at 110° C. and calcined in air for 6 hours at 700° C.

The contents of vanadium, iron, used as active components, and antimony used as a promoter, contained in the catalyst, which was used for dehydrogenation of ethylbenzene to styrene using carbon dioxide, were 8 wt. %, 1 wt. % and 11 wt. %, respectively, based on the oxides.

The V—Fe—Sb/$ZrO_2$—$Al_2O_3$ catalyst with a spherical shape (100 mL) was placed in a tubular reactor of the reaction apparatus represented in FIG. 2. The catalytic activity was measured in the case of using carbon dioxide as an oxidant at a temperature of from 500° C. to 600° C. After the catalyst was treated with nitrogen for an hour, the temperature was raised at intervals of 25° C. starting from 525° C. and the catalytic activity was determined at each temperature after maintaining each temperature for 10 hours. The weight hourly space velocity (WHSV), i.e., the weight ratio of reactants supplied per unit weight of a catalyst per unit hour, was set to 1 per hour, wherein the molar ratio between carbon dioxide and ethylbenzene was 5:1. The carbon dioxide used was the one discharged from the process of manufacturing ethylene oxide with 95% of purity and the rest were 4% of nitrogen, 0.5% of steam, 0.4% of oxygen and 0.1% or less of impurities. The reactant mixture was reacted under atmospheric pressure and the total partial pressure of ethylbenzene and carbon dioxide was set to 0.75 atm by diluting with nitrogen. The reaction results are summarized in Tables 1 and 2. The conversion rate of carbon dioxide was 40.4% at 550° C. based on ethylbenzene and the molar ratio of products between hydrogen and carbon monoxide was 0.78.

COMPARATIVE EXAMPLE 1

The catalytic activity in the dehydrogenation process of ethylbenzene using steam as a diluent was measured in the same manner as in Example 1. The ratio between steam and ethylbenzene was 5:1. The reaction results are summarized in Table 1.

TABLE 1

Reaction results in the presence of V—Fe—Sb/$ZrO_2$—$Al_2O_3$ catalyst

| | Ex 1 (Using carbon dioxide) | | Comp. Ex. 1 (Using steam) | |
|---|---|---|---|---|
| Reaction temp. (° C.) | Ethylbenzene Conversion (%) | Styrene Selectivity (%) | Ethylbenzene Conversion (%) | Styrene Selectivity (%) |
| 525 | 61.7 | 96.1 | 17.6 | 87.3 |
| 550 | 74.1 | 96.9 | 29.5 | 88.7 |
| 575 | 84.4 | 96.6 | 41.2 | 86.6 |
| 600 | 90.8 | 95.7 | 61.6 | 89.1 |

The above Table 1 shows that the styrene selectivity for using carbon dioxide was 6–10% higher and the conversion of ethylbenzene was 30% higher at each temperature than those with using steam in the dehydrogenation reaction of ethylbenzene, respectively.

COMPARATIVE EXAMPLE 2

A Ce—K—$Fe_2O_3$ oxide comprising 83.2 wt. % of $Fe_2O_3$, 9.8 wt. % of $K_2O$, 4.9 wt. % of $Ce_2O_3$, and 2.1 wt. % of CaO, which was 3 mm in diameter and 15 mm in length and had a similar composition to the commercial catalyst used in the dehydrogenation process of ethylbenzene with steam, was utilized herein. The ratio between steam and ethylbenzene was 10:1. The reaction results are summarized in Table 2.

Table 2 shows the results obtained from Example 1 and Comparative Example 2. The catalytic activities in the dehydrogenation of ethylbenzene using carbon dioxide were measured at each temperature and were compared to those using steam. The experimental values of the activities were also compared to theoretical conversions of ethylbenzene obtained from the equilibrium calculation program (HSC Chemistry) designed by Otokumpu Research Co., Ltd. (Finland).

TABLE 2

Reaction results in the presence of V—Fe—Sb/$ZrO_2$—$Al_2O_3$ and Ce—K—$Fe_2O_3$ oxide catalysts

| | V—Fe—Sb/$ZrO_2$—$Al_2O_3$ Using carbon dioxide | | Ce—K—$Fe_2O_3$ Using steam | |
|---|---|---|---|---|
| Reaction temp. (° C.) | Styrene Yield (%) | Theoretical Equilibrium Conversion (%) | Styrene Yield (%) | Theoretical Equilibrium Conversion (%) |
| 525 | 59.3 | 74.0 | 28.1 | 53.5 |
| 550 | 71.8 | 82.0 | 42.2 | 65.0 |
| 575 | 81.5 | 89.5 | 53.9 | 74.0 |
| 600 | 86.9 | 94.5 | 66.0 | 80.0 |

As shown in Tables 1 and 2, when the dehydrogenation was performed using carbon dioxide as an oxidant in the presence of V—Fe—Sb/$ZrO_2$—$Al_2O_3$ catalyst the yield of styrene was 20% higher at all temperatures than that using steam as a diluent in the presence of the Ce—K—$Fe_2O_3$ oxide. The ethylbenzene conversions over V—Fe—Sb/$ZrO_2$—$Al_2O_3$ in the dehydrogenation of ethylbenzene to styrene using carbon dioxide were at least 5% higher than the calculated equilibrium conversion of the dehydrogenation using steam. It is noted that the reaction temperature may be lowered about 50° C. by means of the dehydrogenation of ethylbenzene using carbon dioxide as an oxidant and V—Fe—Sb/$Al_2O_3$ catalyst, as compared to that using steam as a diluent and the Ce—K—$Fe_2O_3$ oxide catalyst.

EXAMPLE 2

In this Example, the dehydrogenation reaction of p-ethyltoluene to p-methylstyrene using carbon dioxide over the same catalyst as Example 1 was performed using the microcatalytic testing unit, wherein a fixed bed reactor made of quartz was vertically installed. The reaction conditions were set as follows: (1) the WHSV was set at 1 per hour; (2) the molar ratio between carbon dioxide and p-ethyltoluene was 20:1; and (3) the reaction temperature was 500° C. The reactant mixture was reacted under atmospheric pressure and the total partial pressure of ethylbenzene and carbon dioxide was set to 0.75 atm by diluting with nitrogen. The conversion of p-ethyl toluene was 39.5% and the selectivity of p-methyl styrene was 95.6%.

COMPARATIVE EXAMPLE 3

The Ce—K—$Fe_2O_3$ oxide used in Comparative Example 2 was applied to the dehydrogenation of p-ethyltoluene using steam as a diluent. Its catalytic activity was measured in the same manner as in Example 2 except the use of the steam diluent and was compared with the activity of Example 2 using carbon dioxide as an oxidant. The molar ratio between steam and p-ethyltoluene was 10:1. The conversion of p-ethyltoluene was 22.7% and the selectivity to p-methylstyrene was 93.3%. It is noted that both the conversion and the selectivity were lower than those in the dehydrogenation using carbon dioxide.

EXAMPLE 3

The dehydrogenation reaction of diethylbenzene was performed using carbon dioxide in the same reaction apparatus using the same catalyst (V—Fe—Sb/$ZrO_2$—$Al_2O_3$) as in Example 2. The reaction conditions were set as follows: (1) the WHSV was set at 1 per hour; (2) the molar ratio between carbon dioxide and diethylbenzene was 1:1; and (3) the reaction temperature was set at 540° C. The conversion of diethylbenzene was 76.1% and the selectivity to divinylbenzenes was 45.4%.

COMPARATIVE EXAMPLE 4

The catalytic activity of the Ce—K—$Fe_2O_3$ oxide used in Comparative Example 2 was applied to the dehydrogenation process of diethylbenzene using steam as a diluent. Its catalytic activity was measured in the same manner as in Example 3 except the use of the steam diluent and was compared with the activity of Example 3 using carbon dioxide as an oxidant. The molar ratio between steam and diethylbenzene was 10:1. The conversion of diethylbenzene was 45.4% and the selectivity of divinylbenzene was 22.5%. It is also noted that both the conversion rate and the selectivity were lower than those in the dehydrogenation using carbon dioxide.

EXAMPLE 4

The dehydrogenation reaction of ethylbenzene was performed in the same manner as in Example 1 except using carbon dioxide-containing gas comprising 50% of carbon dioxide, 5% of steam, 5% of oxygen, and 40% of nitrogen. The conversion of ethylbenzene was 69.9% and the selectivity of styrene was 94.7%.

EXAMPLE 5

The dehydrogenation reaction of ethylbenzene with carbon dioxide as an oxidant was performed in the same method as in Example 2 except that the catalyst used was different. The catalyst used in this Example was prepared in such a manner that the oxides of vanadium, iron and antimony were supported onto metal-modified alumina materials (hereinafter referred to as V—Fe—Sb/M-$Al_2O_3$, where M=metal to modify the $Al_2O_3$ support) via the incipient wetness method. In particular, as a metal to modify the alumina support, one kind of metal was selected from the group consisting of calcium, barium, lanthanum, cerium, yttrium and niobium, and it was added in the amount of 5 wt. %. The contents of vanadium, iron and antimony contained in the catalyst were 25 wt. %, 0.5 wt. % and 12 wt. %, respectively, based on the oxides. Then, it was dried under vacuum for 3 hours at 80° C. and calcined for 6 hours at 700° C.

The dehydrogenation reaction of ethylbenzene was performed by loading of V—Fe—Sb/$La_2O_3$—$Al_2O_3$ catalyst (3 g) into the reactor, wherein the oxides of vanadium, iron and antimony were impregnated onto the lanthania-alumina support. The reaction conditions were set as follows: (1) the WHSV was set at 0.5 per hour; (2) the molar ratio between carbon dioxide and ethylbenzene was 1:1; and (3) the reaction temperature was set at 550° C. The activity of said catalyst after 6 hours on steam was measured and is shown in Table 3. For comparison, the activity of the catalyst using steam is also shown in Table 3.

EXAMPLE 6

The dehydrogenation reaction of ethylbenzene using carbon dioxide was performed in the same manner as in Example 5 except that the catalyst used was different. The catalyst used in this Example was prepared in such a manner that the oxides of vanadium, iron and antimony were supported onto metal-modified zirconia materials (hereinafter referred to as V—Fe—Sb/M—$ZrO_2$, where M=metal to modify the $ZrO_2$ support) via the incipient wetness method. In particular, as a metal to modify the zirconia support, one kind of metal was selected from the group consisting of magnesium, calcium, barium, lanthanum, cerium, yttrium and niobium, and it was added in the amount of 5 wt. %. The contents of vanadium, iron and tin contained in thus prepared V—Fe—Sn/M—$ZrO_2$ catalyst were 12 wt. %, 18 wt. % and 2 wt. %, respectively, based on the oxides.

The dehydrogenation reaction of ethylbenzene was performed by loading of Fe—Sn/CaO—$ZrO_2$ catalyst (3 g) into the reactor, wherein the oxides of vanadium, iron and tin were impregnated in the calcium-zirconia support. The activity of said catalyst after 6 hours on stream was measured and is shown in Table 3. For comparison, the activity of the catalyst using steam is also shown in Table 3.

EXAMPLE 7

The dehydrogenation reaction of ethylbenzene was performed using carbon dioxide same as in Example 5 except that the catalyst used was different. The catalyst used in this Example was prepared in such a manner that the oxides of vanadium and iron were supported onto zirconia-alumina material containing 10 wt. % zirconia (hereinafter referred to as V—Fe/Zr—$Al_2O_3$) via the incipient wetness method. The contents of vanadium and iron contained in thus prepared V—Fe/Zr—$Al_2O_3$ catalyst were 12 wt. % and 2 wt. %, respectively, based on the oxides.

The dehydrogenation reaction of ethylbenzene was performed by loading of V—Fe/Zr—$Al_2O_3$ catalyst (3 g) into a reactor. The activity of said catalyst after 6 hours on stream was measured and is shown in Table 3. For comparison, the activity of the catalyst using steam is also shown in Table 3.

EXAMPLE 8

The dehydrogenation reaction of ethylbenzene was performed using carbon dioxide same as in Example 5 except that the catalyst used was different. The catalyst used in this Example was prepared in such a manner that the oxides of vanadium, iron, and a third metal promoter were impregnated onto alumina support (hereinafter referred to as V—Fe-M/$Al_2O_3$, where M=a third metal). A third metal component as a promoter was selected from the group consisting of potassium, magnesium, lanthanum, chromium, cerium, molybdenum, calcium, manganese, zirconium and cesium. The contents of vanadium, iron and a third metal contained in thus prepared V—Fe-M/$Al_2O_3$ catalyst were 12 wt. %, 7 wt. % and 3 wt. %, respectively, based on the oxides.

The dehydrogenation reaction of ethylbenzene was performed by loading of V—Fe—Cs/$Al_2O_3$ catalyst (3 g) that contains cesium as a metal oxide into a reactor. The activity of said catalyst after 6 hours on stream was measured and is shown in Table 3. For comparison, the activity of the catalyst using steam is also shown in Table 3.

EXAMPLE 9

The dehydrogenation reaction of ethylbenzene was performed using carbon dioxide same as in Example 5 except that the catalyst used was different. In this Example, the catalyst used was prepared by precipitation-deposition method, wherein mixed metal oxides of vanadium, iron, and chromium were deposited onto zirconia material using the ammonia solution (hereinafter referred to as V—Fe—Cr/$ZrO_2$). The contents of vanadium, iron and chromium contained in thus prepared V—Fe—Cr/$ZrO_2$ catalyst were 18 wt. %, 3 wt. % and 8 wt. %, respectively, based on the oxides.

The activity of said catalyst was measured as in Example 5 and is shown in Table 3. For comparison, the activity of the catalyst using nitrogen atmosphere is also shown in Table 3.

EXAMPLE 10

The catalyst used in this Example was V—Fe/Mg—Al double layered hydroxide (LDH) prepared by a combination of hydrothermal synthesis and ion-exchange and incipient wetness methods. The Mg—Al LDH material was first produced by conducting a hydrothermal synthesis of a precursor gel mixture for 1 day at 120° C., wherein the mixture was obtained by slowly adding sodium carbonate while stirring a precursor solution of magnesium and aluminum. Then, a vanadium component was exchanged as vanadate anoin into the interlayer of Mg—Al LDH and this material (V/Mg—Al LDH) was calcined in air at 700° C. for 6 hours. And an iron component was added to the V/Mg—Al LDH material by the incipient wetness method. The contents of iron, vanadium, magnesium and aluminum contained in thus prepared V—Fe/Mg—Al LDH catalyst was 5 wt. %, 10 wt. %, 25 wt. % and 60 wt. %, respectively, based on the oxides. The activity of said catalyst was measured as in Example 5 and is shown in Table 3. For comparison, the activity of the catalyst using nitrogen atmosphere is also shown in Table 3.

EXAMPLE 11

The catalyst used in this Example was prepared in such a manner that iron, vanadium, manganese and tin were impregnated onto titanium dioxide-zirconia material, which was prepared by using a sol-gel method [$TiO_2$: $ZrO_2$=30:70 (molar ratio)], in the amount of 15 wt. %, 1 wt. %, 5 wt. % and 5 wt. %, respectively, based on the oxides. The activity of dehydrogenation of thus prepared Fe—V—Mn—Sn/$TiO_2$—$ZrO_2$ catalyst after 6 hours on stream was measured as in Example 5 and is shown in Table 3. For comparison, the activity of the catalyst using nitrogen atmosphere is also shown in Table 3.

EXAMPLE 12

Fe—V—Cr—Mg—Zr—Al composite catalyst comprising iron, vanadium, chromium, magnesium, zirconium, and aluminum was prepared in this Example by using a sol-gel method and a successive impregnation. The contents of iron, vanadium, chromium, magnesium, zirconium, and aluminum contained in thus prepared Fe—V—Cr—Mg—Zr—Al composite catalyst were 14 wt. %, 16 wt. %, 5 wt. %, 10 wt. %, 35 wt. % and 20 wt. %, respectively, based on the oxides, respectively, based on the oxides. The activity of thus prepared Fe—V—Cr—Mg—Zr—Al composite catalyst after 6 hours on stream was measured as in Example 5 and is shown in Table 3. For comparison, the activity of the catalyst using nitrogen atmosphere is also shown in Table 3.

COMPARATIVE EXAMPLE 5

A K—$Fe_2O_3$ oxide catalyst, similar to an industrial catalyst used in ethylbenzene dehydrogenation using steam, was prepared by the co-precipitation method and calcined at 600° C. for 4 hours. The contents of iron and potassium in the catalyst were 77 wt. % and 23 wt. % as the oxides, respectively. The activity of thus prepared catalyst after 6 hours on stream was measured as in Example 5 and is shown in Table 3. For comparison, the activity of the catalyst using nitrogen atmosphere is also shown in Table 3.

As shown in Table 3, ethylbenzene conversion and styrene yield were shown much higher in the presence of carbon dioxide than under the nitrogen atmosphere, respectively, thus showing that the activity of ethylbenzene dehydrogenation becomes higher in the presence of carbon dioxide than under the nitrogen atmosphere. Further, the K—$Fe_2O_3$ oxide catalyst used in Comparative Example 5 were shown to have much reduced catalytic activity K—$Fe_2O_3$ in the presence of carbon dioxide rather than under the nitrogen atmosphere.

TABLE 3

| | | Using Carbon dioxide | | Using Nitrogen Diluent | |
| --- | --- | --- | --- | --- | --- |
| Classification | Catalyst | Ethylbenzene Conversion (%) | Styrene Yield (%) | Ethylbenzene Conversion (%) | Styrene Yield (%) |
| Example 5 | V—FeSb/ $La_2O_3$— $Al_2O_3$ | 69.1 | 67.0 | 50.2 | 48.2 |

TABLE 3-continued

|  |  | Using Carbon dioxide | | Using Nitrogen Diluent | |
| --- | --- | --- | --- | --- | --- |
| Classification | Catalyst | Ethylbenzene Conversion (%) | Styrene Yield (%) | Ethylbenzene Conversion (%) | Styrene Yield (%) |
| Example 6 | V—FeSn/CaO—ZrO$_2$ | 62.8 | 60.6 | 43.4 | 41.7 |
| Example 7 | V—Fe/Zr—Al$_2$O$_3$ | 65.5 | 63.3 | 42.3 | 40.9 |
| Example 8 | V—Fe—Cs/Al$_2$O$_3$ | 66.1 | 63.7 | 52.1 | 50.3 |
| Example 9 | V—Fe—Cr/ZrO$_2$ | 67.0 | 64.5 | 49.4 | 47.8 |
| Example 10 | V—Fe/Mg—Al LDH | 64.2 | 61.6 | 48.6 | 46.9 |
| Example 11 | Fe—V—Mn—Sn/TiO$_2$—ZrO$_2$ | 64.5 | 62.6 | 40.9 | 39.5 |
| Example 12 | Fe—V—Cr—Mg—Zr—Al | 61.7 | 59.9 | 43.1 | 41.8 |
| Comp. Ex. 5 | K—Fe$_2$O$_3$ | 12.3 | 11.5 | 30.1 | 29.1 |

EXAMPLE 13

The catalytic activity of the catalyst prepared in Example 1 was compared with the supported iron oxide catalyst, the supported vanadium oxide catalysts (V/Al$_2$O$_3$ and V/active carbon) and the physical mixture of these catalysts. The supported iron oxide catalyst, as a comparative catalyst, was prepared so that 15 wt. % of iron oxide is impregnated onto the alumina support using the incipient wetness method (Fe/Al$_2$O$_3$), while the vanadium oxide impregnated catalyst, as a comparative catalyst, was a V/Al$_2$O$_3$ or a V/C (active carbon) catalyst wherein 20 wt. % of vanadium oxide is impregnated onto the alumina or active carbon support using the incipient wetness method.

The activity of the V—Fe—Sb/ZrO$_2$—Al$_2$O$_3$ catalyst prepared in Example 1 and comparative catalysts of Fe/Al$_2$O$_3$ and Fe/Al$_2$O$_3$ were compared according to time-on-stream by performing dehydrogenation after loading 3 g each of the above catalysts to a reactor, wherein the WHSV was 1.5 per hour, the reaction temperature was 550° C. and the molar ratio between carbon dioxide and ethylbenzene was 1:1. The catalytic activities after 6 hours and 20 hours and the degree of deactivation (%) after 20 hours were compared with that after 6 hours and the result is shown in Table 4.

TABLE 4

|  | Styrene Yield (%) | | |
| --- | --- | --- | --- |
| Catalyst | After 6 hours of Reaction | After 20 hours of Reaction | *Degree of catalyst deactivation (%) |
| V—Fe—Sb/ZrO$_2$—Al$_2$O$_3$ | 51.3 | 48.8 | 0.95 |
| Fe/Al$_2$O$_3$ | 30.2 | 15.7 | 0.52 |
| V/Al$_2$O$_3$ | 37.5 | 18.2 | 0.49 |
| V/Carbon | 22.5 | 9.7 | 0.43 |
| Fe/Al$_2$O$_3$ + V/Al$_2$O$_3$ (1:1 physical mixture) | 31.6 | 17.4 | 0.55 |
| Fe/Al$_2$O$_3$ + V/Carbon (1:1 physical mixture) | 31.9 | 14.4 | 0.45 |

*Degree of catalyst deactivation (%) = (Styrene yield after 20 hours/Styrene yield after 6 hours) × 100

The catalyst, wherein iron oxide or vanadium oxide alone is impregnated onto the alumina support, the level of catalytic deactivation drastically increased according to time-on-stream in the presence of carbon dioxide thus the catalytic activity 20 hours after the reaction decreased to approximately half of that of 6 hours after the reaction, whereas the activity of the V—Fe—Sb/ZrO$_2$—Al$_2$O$_3$ catalyst remained stable. The causes of the catalytic deactivation are mainly ascribed to blockage of coke catalytic active sites during the reaction and the over-reduction of vanadium oxide or iron oxide. The results of thermogravimetric analysis of the catalysts collected 20 hours after the reaction revealed that there was only 0.07 g of coke formed per 1 g of V—Fe—Sb/ZrO$_2$—Al$_2$O$_3$ catalyst while there were 0.43 g and 0.39 g of coke formed per 1 g of Fe/Al$_2$O$_3$ catalyst and V/Al$_2$O$_3$ catalyst, respectively, thus showing that the coking phenomenon is greatly related to the catalytic deactivation. Further, iron oxide or vanadium oxide alone cannot maintain its active oxidation state to be stable during the reaction and this leads to the remarkable decrease in catalytic activity. For example, in the active carbon-supported vanadium catalyst the reduction of vanadium oxide becomes more severe than other catalysts, as demonstrated by the surface analysis via x-ray photoelectron spectroscopy, thus showing that the catalytic deactivation became much serious as compared to alumina support. However, when using vanadium oxide along with iron oxide or a third promoter, as in the present invention, it becomes easier to maintain optimum oxidation state, as compared to the cases when iron oxide or vanadium oxide is used alone, thus enabling to prevent deterioration of catalytic activity even for a long period of the reaction.

As described above, it was found that the dehydrogenation of alkylaromatic hydrocarbons according to the present invention inhibits the catalyst deactivation, enhances the conversion of alkylaromatic hydrocarbons and the selectivity of their corresponding alkenylaromatic hydrocarbons, and lowers the reaction temperature when the dehydrogenation is performed by using carbon dioxide, which is directly released from petrochemical processes without any purification process as well as using highly pure carbon dioxide, thus being useful for industrial applications.

What is claimed is:

1. A method for the catalytic dehydrogenation of alkylaromatic hydrocarbons comprising
reacting the alkylaromatic hydrocarbons with carbon dioxide in the presence of a heterogenous solid catalyst comprising vanadium and iron and a catalyst promoter selected from the group consisting of antimony, tin, potassium, magnesium, lanthanum, chromium, cerium, molybdenum, calcium, manganese, zirconium, and cesium oxide, wherein
said heterogenous solid catalyst being associated with a support, selected from the group consisting of alumina, zirconia, metal-modified alumina and metal-modified zirconia said heterogenous solid catalyst being from about 0.1 to about 30 weight % of vanadium and from about 0.1 to about 30 weight % of iron, relative to the total weight of the heterogeneous solid catalyst and support;

said vanadium and iron being active components; and said carbon dioxide functions as an oxidant.

2. The method for catalytic dehydrogenation of alkylaromatic hydrocarbons of claim 1, wherein the metals that modify said alumina support are selected from the group consisting of magnesium, calcium, barium, zirconium, lanthanum, cerium, yttrium and niobium.

3. The method for catalytic dehydrogenation of alkylaromatic hydrocarbons of claim 1, wherein the metals that modify said zirconia support are selected from the group consisting of magnesium, calcium, barium, lanthanum, cerium, yttrium, titanium and niobium.

4. The method for catalytic dehydrogenation of alkylaromatic hydrocarbons of claim 1, wherein said promoter is less than 30 wt. %, relative to the total weight of said heterogeneous solid catalyst.

5. The method for catalytic dehydrogenation of alkylaromatic hydrocarbons of claim 1, wherein said carbon dioxide is chosen from a product of high purity and a crude product discharged in the petrochemical processes.

6. The method for catalytic dehydrogenation of alkylaromatic hydrocarbons of claim 5, wherein said petrochemical process is a process for manufacturing ethylene oxide.

7. The method for catalytic dehydrogenation of alkylaromatic hydrocarbons of claim 5, wherein the concentration of carbon dioxide contained in said crude carbon dioxide is from 50% to 99.9%.

8. The method for catalytic dehydrogenation of alkylaromatic hydrocarbons of claim 1, wherein the molar ratio of said carbon dioxide to the alkylaromatic hydrocarbon ranges from 0.5:1–20:1.

9. The method for catalytic dehydrogenation of alkylaromatic hydrocarbons of claim 1, wherein said heterogeneous solid catalyst is affixed to the surface of said support.

10. The method for catalytic dehydrogenation of alkylaromatic hydrocarbons of claim 1, wherein said heterogeneous solid catalyst is incorporated into said support.

* * * * *

UNITED STATES PATENT AND TRADEMARK OFFICE
CERTIFICATE OF CORRECTION

PATENT NO. : 6,958,427 B2
DATED : October 25, 2005
INVENTOR(S) : Sang-Eon Park et al.

It is certified that error appears in the above-identified patent and that said Letters Patent is hereby corrected as shown below:

<u>Title page,</u>
Item [75], Inventor, add -- Jin S. Yoo, (U.S.A.) --.

Signed and Sealed this

Seventeenth Day of January, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,958,427 B2 | Page 1 of 1 |
| APPLICATION NO. | : 10/376322 | |
| DATED | : October 25, 2005 | |
| INVENTOR(S) | : Sang-Eon Park et al. | |

It is certified that error appears in the above-identified patent and that said Letters Patent is hereby corrected as shown below:

<u>Title page:</u>
Item 57, Abstract, line 7, "improve" should read --improved--.

Claim 1, column 14, line 67, "heterogenous" should read --heterogeneous--

Claim 1, column 15, line 7, "heterogenous" should read --heterogeneous--

Claim 1, column 15, line 8, "support, selected" should read --support selected--

Claim 1, column 15, line 10, "zirconia said" should read --zirconia, said--

Claim 1, column 15, line 10, "heterogenous" should read --heterogeneous--.

Signed and Sealed this

First Day of August, 2006

JON W. DUDAS
*Director of the United States Patent and Trademark Office*